(12) United States Patent
Mauldin, Jr. et al.

(10) Patent No.: US 9,579,120 B2
(45) Date of Patent: Feb. 28, 2017

(54) ULTRASOUND FOR LOCATING ANATOMY OR PROBE GUIDANCE

(75) Inventors: F. William Mauldin, Jr., Charlottesville, VA (US); Francesco Viola, Charlottesville, VA (US); William F. Walker, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/574,738

(22) PCT Filed: Jan. 28, 2011

(86) PCT No.: PCT/US2011/022984
§ 371 (c)(1),
(2), (4) Date: Jul. 23, 2012

(87) PCT Pub. No.: WO2011/094585
PCT Pub. Date: Aug. 4, 2011

(65) Prior Publication Data
US 2012/0296213 A1    Nov. 22, 2012

Related U.S. Application Data

(60) Provisional application No. 61/299,506, filed on Jan. 29, 2010, provisional application No. 61/309,628, (Continued)

(51) Int. Cl.
*A61B 8/00*    (2006.01)
*A61B 17/34*    (2006.01)
*A61B 8/08*    (2006.01)

(52) U.S. Cl.
CPC ........ *A61B 17/3403* (2013.01); *A61B 8/0841* (2013.01); *A61B 8/42* (2013.01);
(Continued)

(58) Field of Classification Search
CPC ... A61B 8/0841; A61B 8/0875; A61B 8/4272; A61B 8/4254; A61B 2017/3413; A61B 17/3403; A61B 2019/5276
(Continued)

(56) References Cited

U.S. PATENT DOCUMENTS 4,363,326 A    12/1982  Kopel
5,259,386 A *  11/1993  Sharkawy ............ A61B 8/0841
                                                              600/455
(Continued)

FOREIGN PATENT DOCUMENTS

CN    102008318 A    4/2011
EP    0891743 A1     1/1999
(Continued)

OTHER PUBLICATIONS

Windows Media File, "Project Lumbar" submitted herewith in electronic form on compact disc, and believed posted on www.youtube.com on Dec. 1, 2009, (Dec. 1, 2009).
(Continued)

*Primary Examiner* — Katherine Fernandez
*Assistant Examiner* — Ellsworth Weatherby
(74) *Attorney, Agent, or Firm* — Schwegman Lundberg & Woessner, P.A.

(57)    ABSTRACT

A hand-held apparatus can be used to assist in guiding a probe or locating a particular anatomical target in a subject. The apparatus can include an ultrasonic transducer located on or within a housing and configured to generate ultrasonic energy directed into tissue of a subject and configured to receive a portion of the ultrasonic energy reflected by a target located within the tissue. In an example, the apparatus can include a motion tracking circuit configured to provide information indicative of a motion of the hand-held apparatus to the processor circuit, and a display configured to
(Continued)

present information about a location of the target with respect to a portion of the hand-held apparatus, the information about the location determined by the processor circuit using the obtained information indicative of the ultrasonic energy reflected by the target and the information indicative of the motion of the hand-held apparatus.

15 Claims, 8 Drawing Sheets

Related U.S. Application Data filed on Mar. 2, 2010, provisional application No. 61/316,989, filed on Mar. 24, 2010.

(52) U.S. Cl.
CPC .......... *A61B 8/4254* (2013.01); *A61B 8/4281* (2013.01); *A61B 17/3401* (2013.01); *A61B 46/10* (2016.02); *A61B 2017/3413* (2013.01); *A61B 2034/2048* (2016.02); *A61B 2090/378* (2016.02)

(58) Field of Classification Search
USPC .......................... 600/446, 461, 462, 463, 466
See application file for complete search history.

(56) References Cited

U.S. PATENT DOCUMENTS

| | | | |
|---|---|---|---|
| 5,546,949 A | 8/1996 | Frazin et al. | |
| 5,623,931 A | 4/1997 | Wung et al. | |
| 5,655,535 A | 8/1997 | Friemel et al. | |
| 5,685,308 A | 11/1997 | Wright et al. | |
| 5,722,412 A | 3/1998 | Pflugrath et al. | |
| 5,782,766 A | 7/1998 | Weng et al. | |
| 5,806,521 A | 9/1998 | Morimoto et al. | |
| 5,833,627 A | 11/1998 | Shmulewitz et al. | |
| 5,924,992 A | 7/1999 | Park et al. | |
| 5,957,844 A | 9/1999 | Dekel et al. | |
| 6,106,464 A * | 8/2000 | Bass et al. ................ | 600/439 |
| 6,203,498 B1 | 3/2001 | Bunce et al. | |
| 6,296,614 B1 | 10/2001 | Pruter | |
| 6,338,716 B1 | 1/2002 | Hossack et al. | |
| 6,641,537 B2 | 11/2003 | Morris et al. | |
| 6,656,136 B1 | 12/2003 | Weng et al. | |
| 6,692,439 B1 | 2/2004 | Walker et al. | |
| 6,733,458 B1 | 5/2004 | Steins et al. | |
| 6,964,639 B2 * | 11/2005 | Sela et al. ................ | 600/443 |
| 7,244,234 B2 | 7/2007 | Ridley et al. | |
| 7,402,136 B2 | 7/2008 | Hossack et al. | |
| 7,578,819 B2 | 8/2009 | Bleich et al. | |
| 7,645,238 B2 | 1/2010 | Hirsh | |
| 7,699,776 B2 | 4/2010 | Walker et al. | |
| 7,750,537 B2 | 7/2010 | Hossack et al. | |
| 7,806,823 B2 | 10/2010 | Sakai et al. | |
| 2003/0073895 A1 | 4/2003 | Nields et al. | |
| 2004/0127790 A1* | 7/2004 | Lang et al. ................ | 600/438 |
| 2004/0158154 A1* | 8/2004 | Hanafy et al. ............. | 600/446 |
| 2005/0016044 A1 | 1/2005 | Kubicek et al. | |
| 2005/0096543 A1 | 5/2005 | Jackson et al. | |
| 2005/0154302 A1 | 7/2005 | Sela et al. | |
| 2005/0154303 A1 | 7/2005 | Walker et al. | |
| 2005/0228281 A1 | 10/2005 | Nefos | |
| 2006/0052697 A1 | 3/2006 | Hossack et al. | |
| 2006/0064010 A1 | 3/2006 | Cannon, Jr. et al. | |
| 2006/0100516 A1 | 5/2006 | Hossack et al. | |
| 2006/0206178 A1 | 9/2006 | Kim | |
| 2006/0264745 A1 | 11/2006 | Da Silva | |
| 2007/0016022 A1 | 1/2007 | Blalock et al. | |
| 2007/0016030 A1 | 1/2007 | Stringer | |
| 2007/0016044 A1 | 1/2007 | Blalock et al. | |
| 2007/0034731 A1 | 2/2007 | Falco | |
| 2007/0073155 A1* | 3/2007 | Park et al. ................ | 600/461 |
| 2007/0156126 A1 | 7/2007 | Flaherty | |
| 2007/0213616 A1 | 9/2007 | Anderson et al. | |
| 2008/0004481 A1 | 1/2008 | Bax et al. | |
| 2008/0015442 A1* | 1/2008 | Watson et al. ............. | 600/459 |
| 2008/0091678 A1 | 4/2008 | Walker et al. | |
| 2009/0043205 A1 | 2/2009 | Pelissier et al. | |
| 2009/0142741 A1 | 6/2009 | Ault et al. | |
| 2009/0143674 A1 | 6/2009 | Nields et al. | |
| 2009/0264757 A1 | 10/2009 | Yang et al. | |
| 2009/0279763 A1 | 11/2009 | Langeland et al. | |
| 2009/0299184 A1 | 12/2009 | Walker et al. | |
| 2009/0304246 A1 | 12/2009 | Walker et al. | |
| 2009/0306509 A1 | 12/2009 | Pedersen et al. | |
| 2010/0010348 A1 | 1/2010 | Halmann | |
| 2010/0016726 A1* | 1/2010 | Meier ......................... | 600/459 |
| 2010/0063399 A1 | 3/2010 | Walker et al. | |
| 2010/0142781 A1 | 6/2010 | Walker et al. | |
| 2010/0168578 A1 | 7/2010 | Garson, Jr. | |
| 2010/0249591 A1 | 9/2010 | Heimdal | |
| 2010/0268086 A1 | 10/2010 | Walker et al. | |
| 2010/0298704 A1 | 11/2010 | Pelissier et al. | |
| 2010/0312120 A1 | 12/2010 | Meier | |
| 2011/0166451 A1 | 7/2011 | Blaivas | |
| 2011/0313288 A1 | 12/2011 | Chi Sing et al. | |
| 2012/0157834 A1 | 6/2012 | Lazebnik | |
| 2013/0172743 A1 | 7/2013 | Brewer et al. | |
| 2013/0310688 A1 | 11/2013 | Rosen et al. | |
| 2014/0046186 A1 | 2/2014 | Mauldin, Jr. et al. | |
| 2014/0350390 A1 | 11/2014 | Kudavelly et al. | |

FOREIGN PATENT DOCUMENTS

| | | |
|---|---|---|
| EP | 2113192 A1 | 11/2009 |
| GB | 2400176 A | 10/2004 |
| JP | 2010012160 A | 1/2010 |
| JP | 2010527277 A | 8/2010 |
| WO | WO-0101866 A1 | 1/2001 |
| WO | WO-03057000 A2 | 7/2003 |
| WO | WO-03075769 A1 | 9/2003 |
| WO | WO-2004064619 A2 | 8/2004 |
| WO | WO-2004064620 A2 | 8/2004 |
| WO | WO-2004065978 A2 | 8/2004 |
| WO | WO-2005014079 A2 | 2/2005 |
| WO | WO-2006042067 A2 | 4/2006 |
| WO | WO-2007027511 A2 | 3/2007 |
| WO | WO-2007035765 A2 | 3/2007 |
| WO | WO-2008154632 A2 | 12/2008 |
| WO | WO-2010021709 A1 | 2/2010 |
| WO | WO-2010106379 A1 | 9/2010 |
| WO | WO-2011094585 A1 | 8/2011 |
| WO | WO-2012148985 A1 | 11/2012 |
| WO | WO-2015025183 A1 | 2/2015 |

OTHER PUBLICATIONS

Selected screen captures obtained Jul. 19, 2012 from Windows Media File (.WMV) titled "Project Lumbar," submitted herewith, (Jul. 19, 2012), 19 pgs.
"International Application Serial No. PCT/US2011/022984, Search Report mailed Apr. 12, 2011", 15 pgs.
"International Application Serial No. PCT/US2011/022984, Written Opinion mailed Apr. 7, 2011", 15 pgs.
"International Application Serial No. PCT/US2012/034945, International Search Report mailed Aug. 7, 2012", 3 pgs.
"International Application Serial No. PCT/US2012/034945, Written Opinion mailed Aug. 7, 2012", 7 pgs.
"The Signos, Self Contained Handheld Ultrasound Gains FDA Approval", http://medgadget.com/archives/2009/05/the_signos_self_contained_handheld_ultrasound_gains_fda_approval.html, (May 20, 2009), 5 pgs.
"VMUT—Freehand 3D Ultrasound", Virginia Medical Ultrasound Technology Group, [Online]. Retrieved from the Internet: <URL: http://hobbes.ee.virginia.edu/ultra/ibeam.html>, (Accessed Jan. 19, 2011), 1 pg.
Ellis, Michael A, et al., "Super-Resolution Image Reconstruction Using Diffuse Source Models", Ultrasound in Med.& Biol., vol. 36, No. 6, (2010), 967-977.

(56) References Cited

OTHER PUBLICATIONS

Fuller, M. I, et al., "Real time imaging with the Sonic Window: A pocket-sized, C-scan, medical ultrasound device", 2009 IEEE International Ultrasonics Symposium (IUS), (2009), 196-199.
Jensen, J Arendt, et al., "Calculation of Pressure Fields from Arbitrarily Shaped, Apodized, and Excited Ultrasound Transducers", IEEE Transactions on Ultrasonics, Ferroelectrics and Frequency Control vol. 39, No. 2, (Mar. 1992), 262-267.
Karaman, Mustafa, et al., "Synthetic Aperture Imaging for Small Scale Systems", IEEE Transactions on Ultrasonics, Ferroelectrics, and Frequency Control vol. 42, No. 3, (May 1995), 429-442.
Klein, Stephen M, et al., "Piezoelectric Vibrating Needle and Catheter for Enhancing Ultrasound-Guided Peripheral Nerve Blocks", Anesthesia & Analgesia, vol. 105 No. 6, (Dec. 2007), 1858-1860.
O'Donnell, Matthew, "Coded Excitation System for Improving the Penetration of Real-Time Phased-Array Imaging Systems", IEEE Transactions on Ultrasonics, Ferroelectrics, and Frequency Control vol. 39, No. 3, (May 1992), 341-351.
Parmar, Biren J, et al., "Characterization of controlled bone defects using 2D and 3D ultrasound imaging techniques", Physics in Medicine and Biology, vol. 55, (2010), 4839-4859.
Viola, et al., "Time-Domain Optimized Near-Field Estimator for Ultrasound Imaging : Initial 1-40", IEEE Transactions on Medical Imaging 27(1), (Jan. 2008), 99-110.
"U.S. Appl. No. 14/113,672, Preliminary Amendment mailed Oct. 24, 2013", 9 pgs.
"International Application Serial No. PCT/US2011/022984, International Preliminary Report on Patentability mailed Aug. 9, 2012", 8 pgs.
"International Application Serial No. PCT/US2012/034945, International Preliminary Report on Patentability mailed Nov. 7, 2013", 9 pgs.
"SieScape Panoramic Imaging Expanding your field of view in real time", Siemens Medical, (2003), 4 pgs.
"Signostics Brochure", (2010), 4 pgs.
"The Minivisor", [Online]. Retrieved from the Internet: <URL: http://www.ob-ultrasound.net/minivisor.html>, (Accessed Jan. 12, 2011), 2 pgs.
Murphy, Kevin P, et al., "Loopy Belief Propagation for Approximate Inference: An Empirical Study", UAI'99 Proceedings of the Fifteenth conference on Uncertainty in artificial intelligence, Computer Science Division, University of California Berkeley, (1999), 467-475.
Woo, Joseph, "A short History of the development of Ultrasound in Obstetrics and Gynecology", Part 2, [Online]. Retrieved from the Internet: <URL: http://www.ob-ultrasound.net/history2.html>, (Accessed Oct. 29, 2013), 32 pgs.

"Chinese Application Serial No. 201180016949.5, Response filed Aug. 7, 2014 to Office Action mailed Mar. 25, 2014", w/ English Translation of Claims, 19 pgs.
"European Application Serial No. 12777556.7, Office Action mailed Dec. 3, 2013", 3 pgs.
"European Application Serial No. 12777556.7, Response filed May 28, 2014 to Office Action mailed Dec. 3, 2013", 10 pgs.
"Chinese Application Serial No. 201180016949.5, Office Action mailed Mar. 25, 2014", With English Version, 27 pgs.
"Chinese Application Serial No. 201180016949.5, Office Action mailed Sep. 18, 2014", w/English Translation, 35 pgs.
"U.S. Appl. No. 14/113,672, Response filed May 27, 2015 to Restriction Requirement mailed Mar. 27, 2015", 8 pgs.
"U.S. Appl. No. 14/113,672, Restriction Requirement mailed Mar. 27, 2015", 7 pgs.
"U.S. Appl. No. 14/113,672, Final Office Action mailed Feb. 1, 2016", 13 pgs.
"U.S. Appl. No. 14/113,672, Response filed Oct. 16, 2015 to Non Final Office Action mailed Jul. 16, 2015", 11 pgs.
"U.S. Appl. No. 14/113,672, Response filed Apr. 1, 2016 to Final Office Action mailed Feb. 1, 2016", 11 pgs.
"European Application Serial No. 12777556.7, Response filed Feb. 29, 2016", 16 pgs.
"Japanese Application Serial No. 2014-508505, Office Action mailed Mar. 15, 2016", w/ English Translation, 9 pgs.
"Japanese Application Serial No. 2014-508505, Response filed Jun. 8, 2016 to Office Action mailed Mar. 15, 2016", with English translation of claims, 11 pgs.
"U.S. Appl. No. 14/113,672, Non Final Office Action mailed Sep. 6, 2016", 21 pgs.
Basarab, "Two-dimensional least-squares estimation for motion tracking in ultrasound elastography". Proceedings of the 29th Annual International Conference of the IEEEE MBS Cite Internationale, (2007).
Chen, "Ultrasound Guided Spine Needle Insertion", Medical Imaging 2010: Visualization, Image-GuidedProcedures, and Modeling, Proc. of SPIE vol. 7625, (2010), 8 pgs.
Cootes, T. F., et al., "Active Shape Models- Their Training and Application". Computer Vision and Image Understanding, vol. 61, (1995), 38-59 pgs.
Khallaghi, "Registration of a Statistical Shape Model of the Lumbar SPine to 3D Ultrasound Images", Medical Image Computing and Computer- Assisted Intervention—MICCAI 2010, vol. 6362 of the series Lecture Notes in Computer Science, (2010), 68-75 pgs.
Wachinger, "Estimation of acoustic impedance from multiple ultrasound images with application to spatial compounding", Computer Vision and Pattern Recognition Workshops, (2008), 8 pgs.
"U.S. Appl. No. 14/113,672, Non Final Office Action mailed Jul. 16, 2015", 17 pgs.
"European Application Serial No. 12777556.7, Extended European Search Report mailed Aug. 13, 2015", 12 pgs.

* cited by examiner

ULTRASOUND FOR LOCATING ANATOMY OR PROBE GUIDANCE

CLAIM OF PRIORITY

This patent application is a U.S. National Stage Filing under 35 U.S.C. §371 from International Patent Application Serial No. PCT/US2011/022984, filed on Jan. 28, 2011, and published as WO 2011/094585A1 on Aug. 4, 2011, which claims the benefit of priority, under 35 U.S.C. Section 119(e), to Mauldin et al., U.S. Provisional Patent Application Ser. No. 61/299,506 entitled "Ultrasound-Based Medical Device and Related Method for Locating Anatomy and/or Guiding a Probe to a Target," filed on Jan. 29, 2010, and to Mauldin et al., U.S. Provisional Patent Application Ser. No. 61/309,628 entitled "Ultrasound-Based Medical Device and Related Method for Locating Anatomy and/or Guiding a Probe to a Target," filed on Mar. 2, 2010, and to Mauldin et al., U.S. Provisional Patent Application Ser. No. 61/316,989 entitled "Ultrasound-Based Medical Device and Related Method for Locating Anatomy and/or Guiding a Probe to a Target," filed on Mar. 24, 2010, the benefit of priority of each of which is claimed hereby, and each of which are incorporated by reference herein in its entirety.

BACKGROUND

Various medical procedures can include penetrating the skin with a probe, such as a needle or a catheter. For example, spinal anesthesia or a spinal diagnostic procedure can include percutaneous delivery of anesthetic to an epidural location or sampling of spinal fluid. Such spinal anesthesia or spinal diagnostic procedures generally include penetrating the ligamentum flavum, a ligament between the spinous processes lateral to the dura. Generally, a desired final needle position during epidural placement is lateral the dura, while in a spinal tap, the dura is penetrated in order to obtain fluid from the spinal cavity.

Spinal taps have several important clinical applications including sampling cerebral spinal fluid (CSF), administering chemotherapy or other drugs directly into the spinal cavity, or relieving pressure in the spinal cavity for cardiac procedures. Sampling of CSF can also be necessary to quickly diagnose various diseases such as meningitis. Other procedures can similarly include penetrating the skin with a probe, such as paravertebral somatic nerve blockade (PVB).

OVERVIEW

During a medical procedure, a probe insertion can sometimes be accomplished without requiring medical imaging (e.g., using an unguided technique). However, such unguided techniques can sometimes fail. For example, in a spinal anesthesia or a spinal diagnostic procedure, failure can prevent access to the spinal cavity, or preclude placement of a needle or catheter lateral the dura for administration of an epidural. Unguided spinal anesthesia or a spinal diagnostic procedure failures typically occur in the elderly or morbidly obese. Reasons for failure in unguided procedures include incorrect needle insertion location or use of an incorrect needle angle during penetration.

Failures due to "blind" or unguided procedures can occur at rates as high as 40% of all cases, and in 74% of cases involving obese patients. Such failures can increase healthcare costs, such as causing complications requiring additional treatment. Such complications can include spinal headaches, back pain, paraparesis, spinal hematoma, nerve palsy, spinal tumor formation, or one or more other complications.

In the morbidly obese such failure can occur because anatomical landmarks, such as spinous process or hip bones cannot be reliably palpated due to thick layers of fatty tissue between the landmarks and the skin, for example. Generally, when the unguided approach fails, clinical procedure includes using fluoroscopy or ultrasound-guided procedures to assist in probe placement. Ultrasound systems currently in use are generally large, complicated, and expensive, requiring specialized training to operate. Fluoroscopy can be undesirable due to the ionizing nature of radiation used during the fluoroscopic imaging procedure.

The present inventors have recognized, among other things, that a self-contained hand-held ultrasound apparatus can be used to guide a probe to a desired location within a subject (e.g., a patient), such as providing information about a location of one or more targets within the subject, instead of using generally-available B-mode ultrasound imaging or fluoroscopy. Such a hand-held apparatus can be simpler to operate than generally available ultrasound imaging equipment. For example, information provided by the hand-held apparatus can be simpler to interpret, in contrast to generally-available B-mode ultrasonic imaging equipment.

Such a hand-held apparatus can enable more accurate and less-resource consuming puncture or probe insertion procedures, for example, such as providing information to the user about a depth or location of bone with respect to a portion of a hand-held assembly, without requiring interpretation of B-mode imaging information by the user. For example, the present inventors have also recognized that a hand-held apparatus can be less expensive than generally-available B-mode imaging equipment. Also, incorporation of display into the hand-held assembly can provide an intuitive or easy-to-understand indication of a bone location or depth, as compared to a B-mode sonogram that can be difficult to interpret. Use of the hand-held apparatus can also reduce medical costs because the hand-held apparatus can be used for guided probe insertion or anatomical location, reducing a likelihood of failure or complication during a probe insertion.

In an example, the hand-held apparatus can include a probe guide configured to provide a specified path for guiding travel by a probe. In an example, a portion of the apparatus, such as including the probe guide, can include a sterile seal configured to isolate the probe, or a portion of the subject, from a non-sterile portion of the hand-held apparatus. The hand-held apparatus can include a display, such as integrated into a hand-held housing of the apparatus, such as to present information to a user such as raw ultrasound data, or a representation of a location of a target, such as a bone location.

In an example, a hand-held apparatus can be used to assist in guiding a probe to a desired location or in locating a particular anatomical target in a subject. The apparatus can include an ultrasonic transducer located on or within a housing, the transducer configured to generate ultrasonic energy directed into tissue of a subject or configured to receive a portion of the ultrasonic energy reflected by a target located within the tissue.

In an example, the apparatus can include a motion tracking circuit configured to provide information indicative of a motion of at least a portion of the hand-held apparatus to the processor circuit, and a display configured to present information about a location of the target with respect to a portion of the hand-held apparatus, the information about the location determined by the processor circuit using the obtained information indicative of the ultrasonic energy reflected by the target and the information indicative of the motion of the hand-held apparatus.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
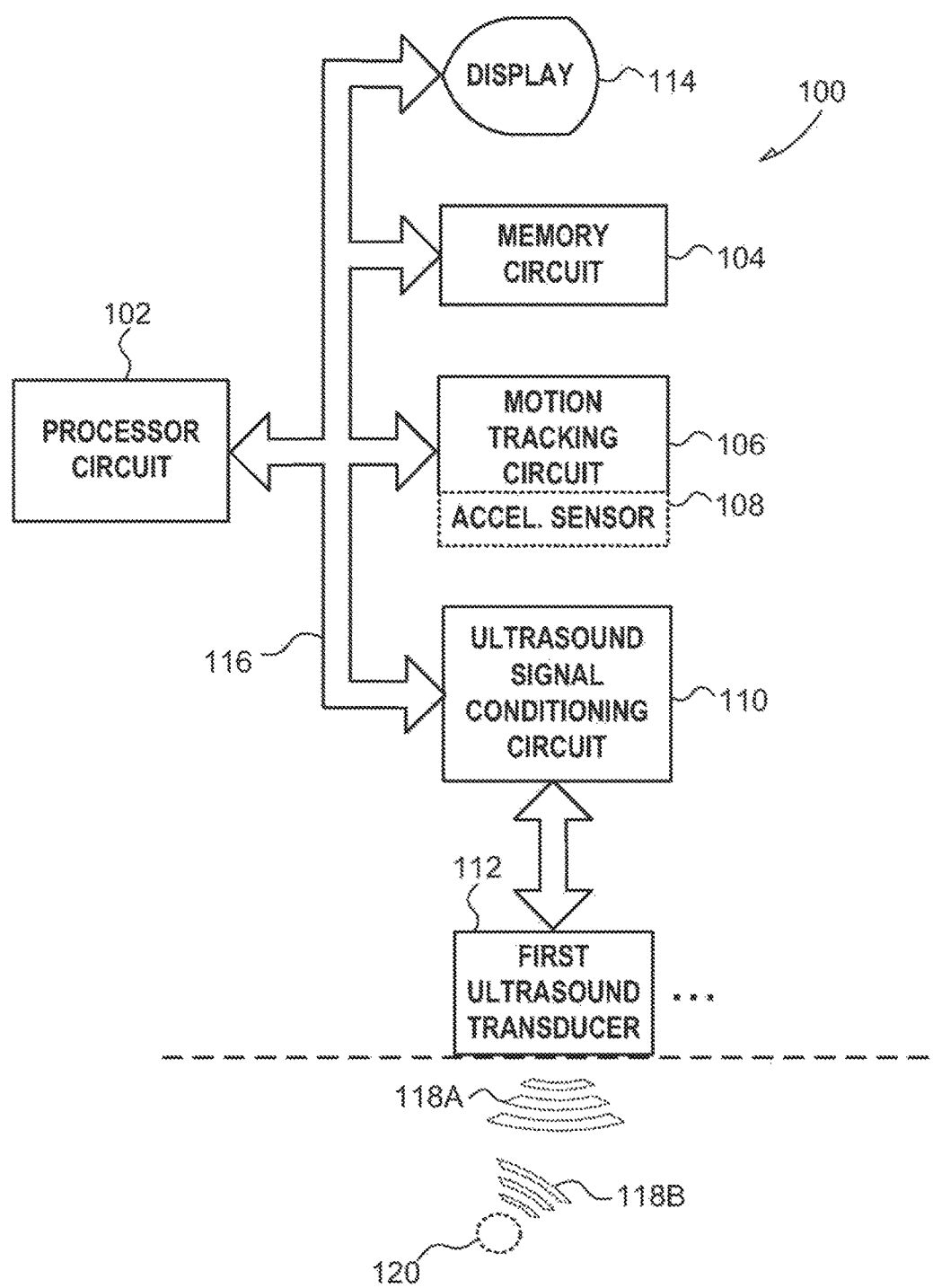
FIG. 1 illustrates generally an example of an apparatus, such as a hand-held apparatus, that can include an ultrasound transducer and a motion tracking circuit.

FIG. 1 illustrates generally an example of an apparatus 100, such as a hand-held apparatus, that can include an ultrasound transducer 112 and a motion tracking circuit 106. In the example of FIG. 1, one or more ultrasound transducers, such as the first ultrasound transducer 112, can generate ultrasonic energy 118A to be directed into a subject (e.g., insonifying a region of interest within the subject). Some of the ultrasonic energy 118A can be reflected by the target 120, such as providing reflected ultrasonic energy 118B. In an example, the ultrasonic transducer 112 can be included as a portion of an ultrasonic transducer array, and can be placed in contact with a surface (e.g., skin) of a patient.

In an example, the reflected ultrasonic energy 118B can be received by the first ultrasonic transducer 112, or by one or more other ultrasonic transducers. The first ultrasonic transducer 112 can be coupled to an ultrasonic signal conditioning circuit 110, such as coupled to a processor circuit 102 or a memory circuit 104 via a bus 116. The ultrasonic signal conditioning circuit 110 can include beam-forming circuitry or other processing circuitry. For example, the ultrasonic signal condition circuit can be configured to amplify, phase-shift, time-gate, filter, or otherwise condition received ultrasonic information (e.g., echo information), such as provided to the processor circuit 102.

For example, the receive path from each element in a transducer array, such as an array including the first ultrasonic transducer 112, can include one or more of a low noise amplifier, a main-stage amplifier, a band-pass or a low-pass filter, or an analog-to-digital converter. In an example, one or more signal conditioning steps can be performed digitally, such as using the processor circuit 102. The term processor is used to generically refer to digital circuitry that can be used to manipulate ultrasound information obtained from the ultrasound transducer 112. Such circuitry can include one or more of a field-programmable gate array (FPGA) or other programmable logic devices (PLDs), a microprocessor, a system-on-chip including one or more execution cores or other circuitry, a microcontroller, or one or more other circuits.

In an example, the apparatus 100 of FIG. 1 can be configured to obtain imaging information from loci corresponding to portions on or nearby an anatomical target of interest, such as a bone (e.g., a portion of the spinous process as shown in the examples below).

In an example, the apparatus 100 can be configured to obtain ultrasonic echo information corresponding to one or more planes perpendicular to the surface of an array of ultrasound transducers (e.g., to provide "B-mode" imaging information). In an example, the apparatus 100 can be configured to obtain information corresponding to one or more planes parallel to the surface of the array of ultrasound transducers (e.g., to provide a "C-mode" ultrasound image of loci in a plane parallel to the surface of the transducer array at a specified depth within the tissue of the subject).

In an example, the processor circuit 102 can be coupled to one or more processor readable media, such as the memory circuit 104, a disk, or one or more other memory technology or storage devices. In an example, a combination of one or more of the first ultrasonic transducer 112, the signal conditioning circuit 110, the processor circuit 102, the memory circuit 104, a display 114, or a user input can be included as a portion of a hand-held ultrasound imaging apparatus. The hand-held apparatus can include one or more piston-type transducers, such as configured to obtain depth information via reflections of ultrasonic energy from an echogenic target such as bone.

In an example, the hand-held apparatus 100 can include apparatus or circuitry such as shown and described in Fuller, M. I., Owen, K., Blalock, T. N., Hossack, J. A., and Walker, W. F., "Real time imaging with the Sonic Window: A pocket-sized, C-scan, medical ultrasound device," 2009 IEEE International Ultrasonics Symposium (IUS), September 2009, pp. 196-199, which is hereby incorporated by reference herein in its entirety, including its discussion of a compact, integrated 60 element×60 element ultrasonic transducer array configured to both insonify tissue and receive echo information from the tissue.

Other examples of apparatus or circuitry that can be included as a portion of the apparatus 100, or one or more techniques that can be used in relation to the apparatus 100, can be found in one or more of Walker, W. F., et al., United States Patent Application Publication US2010/0268086, "Intuitive Ultrasonic Imaging System and Related Method Thereof," or Walker, W. F., et al., United States Patent Application Publication US2010/0063399, "Front End Circuitry for Imaging Systems and Methods of Use," or Hossack, J. A., et al., United States Patent Application Publication US2009/0048519, "Hybrid Dual Layer Diagnostic Ultrasound Transducer Array" (issued as U.S. Pat. No. 7,750,537), or Blalock, T. N., et al., United States Patent Application Publication US 2007/0016044, "Ultrasonic Transducer Drive," or Blalock, T. N., et al., United States Patent Application Publication US2007/0016022, "Ultrasound Imaging Beam-Former Apparatus and Method," or Hossack, J. A., et al., United States Patent Application Publication US2006/0100516, "Efficient Architecture for 3D and Planar Ultrasonic Imaging—Synthetic Axial Acquisition and Method thereof," or Hossack, J. A., et al., United States Patent Application Publication US2006/0052697, "Efficient Ultrasound System for Two-Dimensional C-scan Imaging and Related Method thereof," (issued as U.S. Pat. No. 7,402,136), or Walker, W. F., United States Patent Application Publication US2005/0154303, "Intuitive Ultrasonic Imaging System and Related Method thereof" (issued as U.S. Pat. No. 7,699,776), each of which are hereby incorporated by reference herein in each of their respective entireties.

In an example, the processor circuit 102 (or one or more other processor circuits) can be communicatively coupled to one or more of a user input, or the display 114, such as via the bus 116. For example, the user input can include one or more of a keypad, a keyboard (e.g., located near or on a portion of ultrasound scanning assembly, or included as a portion of a workstation configured to present or manipulate ultrasound imaging information), a mouse, a touch-screen control, a rotary control (e.g., a knob or rotary encoder), or a soft-key aligned with a portion of the display 114, or including one or more other controls.

In an example, the processor circuit 102 can be configured to construct one or more composite images (e.g., a set of two-dimensional or three-dimensional representations of the location, shape, or depth of the target 120), such as using imaging information obtained using the first ultrasonic transducer 112 (or an array), such as shown in the examples of FIGS. 5, 6A-C, or FIG. 7. The processor circuit 102 can present the constructed image to the user via the display 114, such as presenting an image including one or more features or indicia as shown in the examples below. The apparatus can generally include one or more piston-type ultrasonic transducers, such as located on a two-dimensional grid, however, one or more other transducer types can be used.

In an example, information can be obtained or sampled, the information indicative of ultrasonic energy reflected from the target 120 as the apparatus 100 is swept or moved across a range of locations. A composite can be constructed such as using information about the location of at least the transducer 112 of the hand-held apparatus 100 (or the entire apparatus), such as provided by the motion tracking circuit 106, and information about reflected ultrasonic energy obtained by the ultrasonic transducer 112. For example, the motion tracking circuit can include an acceleration sensor 108, such as an accelerometer configured to sense acceleration in one or more axes. The motion tracking circuit 106 can use one or more other techniques to determine a relative motion or absolute position of the apparatus 100, such as using electromagnetic, magnetic, optical, or acoustic techniques, or a gyroscope, such as independently of the received ultrasound imaging information (e.g., without requiring motion tracking based on the position of imaged objects determined according to received ultrasonic information).

Other techniques can include using one or more transducers that can be mechanically scanned, such as to provide imaging information similar to the information provided by a two-dimensional array, but without requiring the user to manually reposition the apparatus 100 during a medical procedure. In such examples, the motion tracking circuit 106 can be used track a location or motion of one or more scanned ultrasonic transducers, such as to provide information for construction of a composite or "mosaic" of depth samples or other imaging information based on received ultrasonic echo information from the transducer during or after it mechanically scanned to two or more locations.

Various examples of the apparatus 100 can be used to partially automate or assist a user in locating anatomy in the spinal region. In the examples of FIGS. 2A-B, 3A-B, or in other examples, a probe guide can be included as a portion of the apparatus to provide a desired or specified probe insertion angle during a medical procedure. For example, the apparatus 100 can improve the accuracy of probe insertion for spinal anesthesia or for spinal diagnostic procedures in difficult patients, particularly the obese, thus reducing instances of multiple needle sticks or eliminating the need for use of fluoroscopy as compared to an unguided procedure.

The apparatus 100 can be small and portable, such that a user (e.g., a physician or nurse) can easily transport it throughout healthcare facilities. The present inventors have also recognized other advantages to the apparatus 100, such as that it can provide imaging using non-ionizing energy, it can be safe, portable, hand-held, low cost, and can provide an apparatus or technique to align a location or insertion angle of a probe to reach a desired target depth or anatomical location.

For example, a purpose-built and designed apparatus can be used such as to determine a depth or location of bone while providing an intuitive display to the user, without requiring interpretation of B-mode sonogram by the user.

Figure 2A:
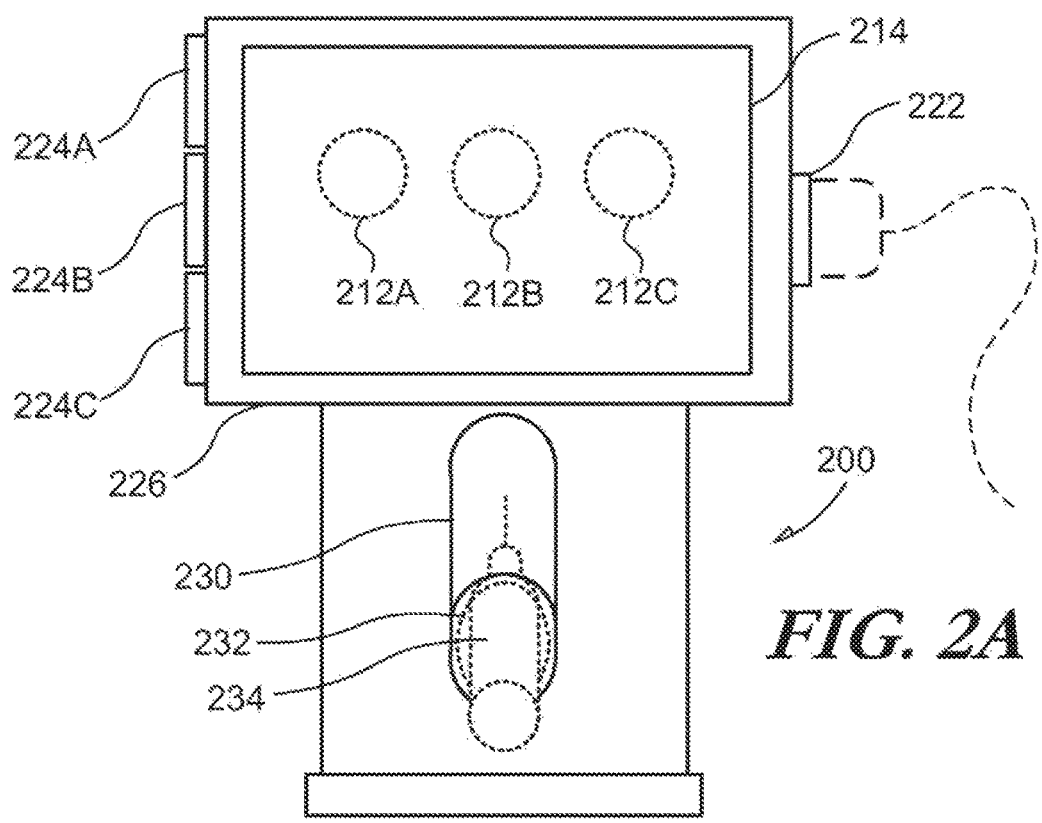
FIGS. 2A-B illustrate generally views of an example of an apparatus, such as including one or more portions of the apparatus of FIG. 1.
Figure 2B:
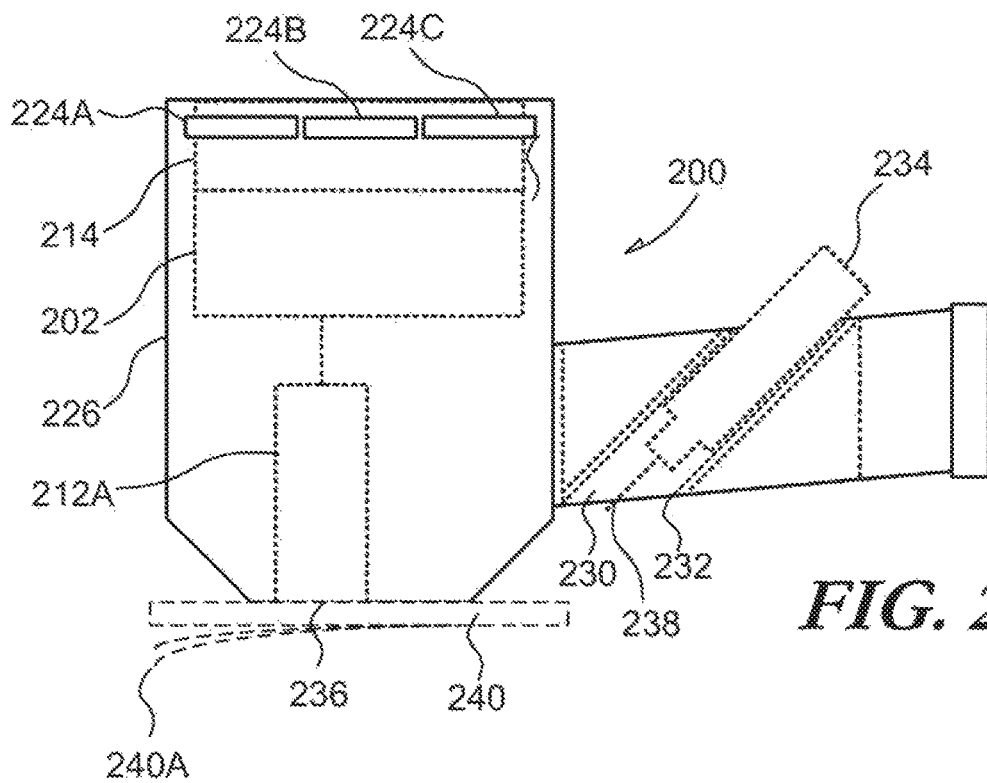

FIGS. 2A-B illustrate generally views of an example of an apparatus 200, such as including one or more portions of the apparatus of FIG. 1. The apparatus 200 can be held-hand, such as sized and shaped for easy manipulation by a user using a single hand. In the examples of FIGS. 2A-B, the apparatus 200 can include one or more ultrasonic transducers, such as a first transducer 212A, a second transducer 212B, or a third transducer 212C. The apparatus 200 can include a display 214, such as included on or within a portion of a housing 226 of the apparatus 200. In an example, the apparatus can include electronic circuitry 202, such as located in a space near the display 214. The electronic circuitry 202 can include one or more portions of the apparatus 100 shown in the example of FIG. 1, such as a processor circuit, a memory circuit, ultrasound signal conditioning circuitry, a motion tracking circuit, or one or more other circuits or modules.

In an example, the apparatus 200 can include a user input, such as discussed above with respect to the examples of FIG. 1, such as including one or more pushbuttons such as a first button 224A, a second button 224B, or a third button 224C, or one or more other input devices. In an example, the apparatus 200 can include either wireless or wired networking or interface capabilities, such as including a wired communication interface port 222 (e.g., a Universal Serial Bus (USB) port, a FireWire port, an Ethernet interface, or one or more other interface technologies), such as for transferring ultrasonic imaging information to a nearby or remote location, or for presentation or review at a nearby or remote workstation.

In an example, the apparatus 200 can include a probe guide 230, such as configured to provide a desired or specified insertion angle for a probe assembly 234, such as including a needle 238 or catheter. In an example, the probe guide 230 can include a removable or replaceable sterile insert or seal 232, such as configured to isolate the probe assembly 234 that can be sterile, from other portions of the apparatus 200 that need not be sterile. In an example, the angle of the probe guide 230 can be adjustable, such as using one or more techniques or apparatus included in the example of FIG. 4.

In an example, an active surface 236 of the apparatus 200 can include a sterile cover 240, such as configured to isolate a non-sterile portion of the apparatus 200 from the patient. In an example, the cover 240 can include one or more peelable or otherwise detachable sheets, such as a first sheet 240A. Thus, the sterility of the apparatus 200 can be more easily maintained in a region touching the skin of the subject. In an example, the sheet 240A can include a template or other target that can be affixed or otherwise adhered to a portion of the subject being imaged, such as to aid a user in keeping track of a desired insertion location for a probe, even after the apparatus 200 is removed. Such a template can include one or more of an insertion location, a graphical outline of spine anatomy (or other anatomy), and indication of a needle path, etc. In an example, one or more portions of the apparatus 200 can be temporarily secured to the subject's skin, such as using an adhesive coating, suction cups, a clamp, or other apparatus.

Figure 3A:
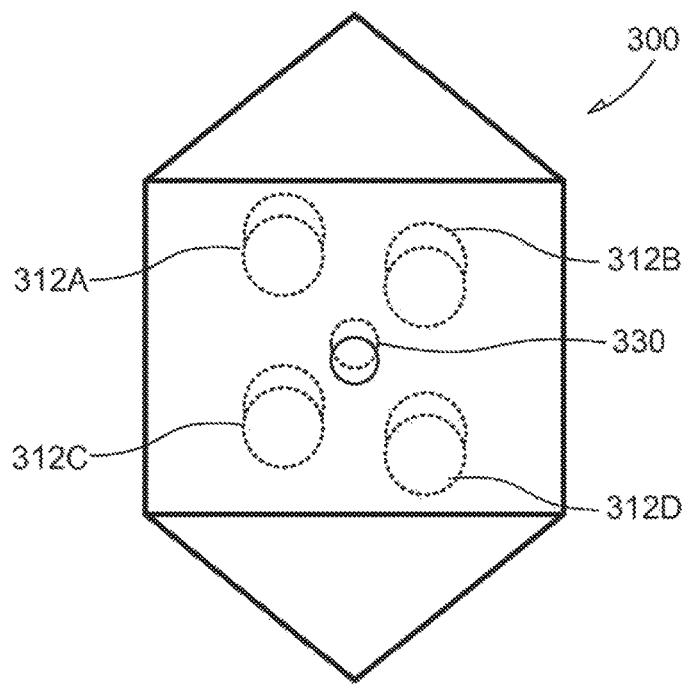
FIGS. 3A-B illustrate generally views of an example of an apparatus, such as including one or more portions of the apparatus of FIG. 1.
Figure 3B:
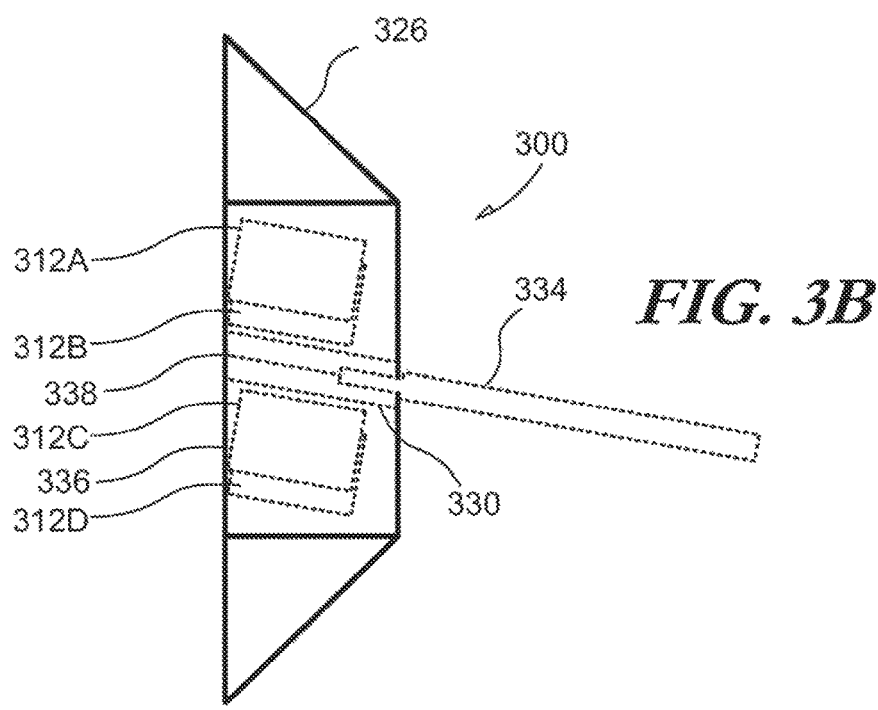
Figure 5:
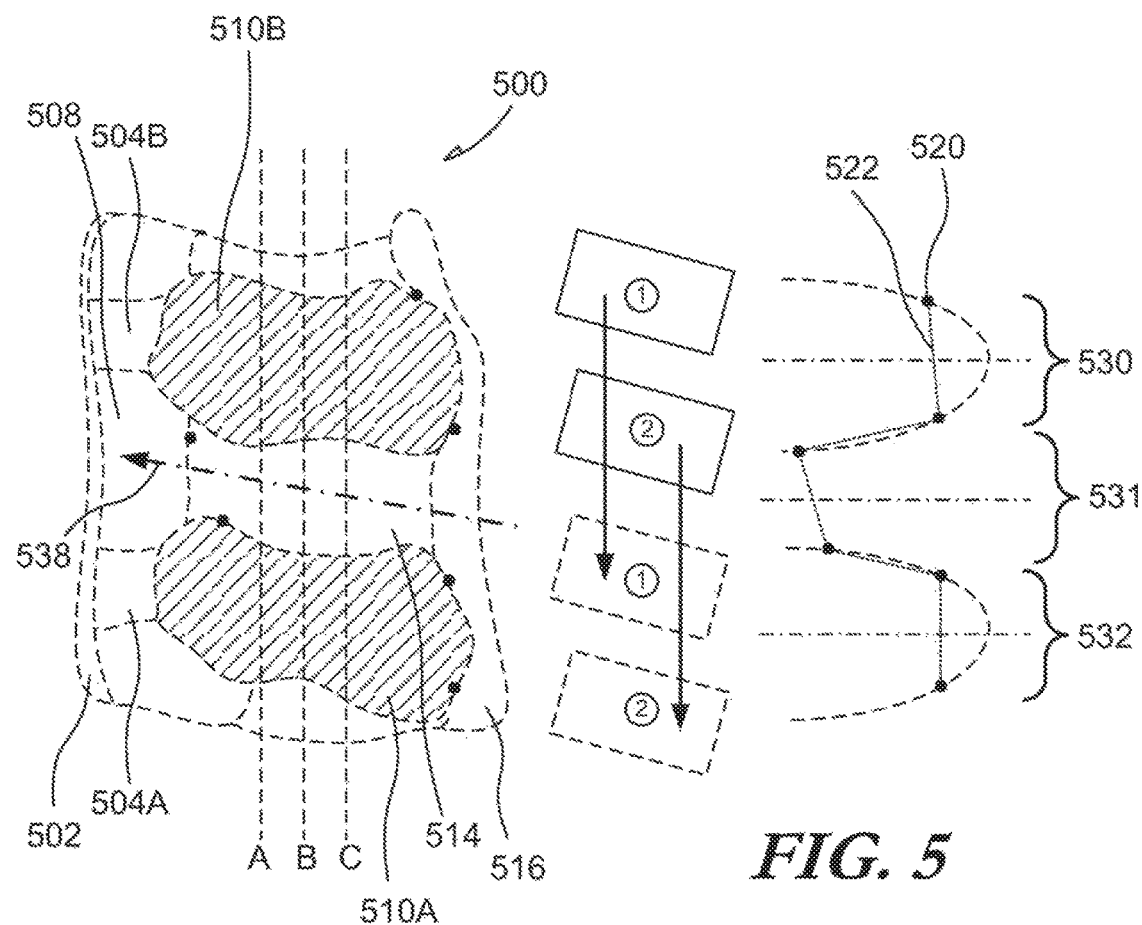
FIG. 5 illustrates generally an illustrative example of obtaining information about one or more portions of an anatomy of a subject, such as to assist in determining an insertion location for a probe, or for guiding a probe to a desired location.

One or more of the ultrasonic transducers 212A-C can be angled, such as to more effectively transmit or receive ultrasonic energy towards a target via an angled path that is neither purely parallel nor purely perpendicular to the plane of the subject's skin, such as shown in the example of FIG. 5, or in the example of the apparatus of FIGS. 3A-B.

In an example, the display 214 can be configured to provide information about a location (e.g., a depth) of a target, such as bone, such as using information obtained during or after the apparatus 200 is moved through two or more locations along the skin of a subject. In an example, information about the target can be obtained via mechanical scanning of one or more of the ultrasonic transducers 212A-C (e.g., linearly, or along a curved path, etc.), such as to form a composite image for presentation to the user via the display 214 without requiring the user to reposition the apparatus 200.

FIGS. 3A-B illustrate generally views of an example of an apparatus 300, such as including one or more portions of the apparatus of FIG. 1. In an example, the apparatus 300 can be included as a portion of the hand-held apparatus 200 of the examples of FIGS. 2A-B. In FIG. 3, one or more ultrasonic transducers can be located on or near a surface 336 of the apparatus 300. The surface 336 can be placed in contact with the skin of a subject, such as for locating, visualizing, or identifying underlying anatomy, such as bone. In the examples of FIGS. 3A-B, a first ultrasonic transducer 312A, a second ultrasonic transducer 312B, a third ultrasonic transducer 312C, or a fourth ultrasonic transducer 312D can be configured to generate ultrasonic energy to be directed into tissue of a subject. For example, one or more transducers 312A-D can be used to determine a depth corresponding to an echogenic portion of a subject, such as bone. Information obtained from the one or more transducers 312A-D can be used to identify a location for insertion of a probe, such as via a path through a probe guide 330 included as a portion of the apparatus 300. One or more of the transducers 312A-D can be configured to transmit in a focused or defocused mode. In an example of focused transmission, the first transducer 312A need not be focused at the same depth as the other transducers 312B-D. In an example, the transmitting transducer need not be the same as the receiving transducer.

In an example, such as shown in FIGS. 5, 6A-C, and 7, information about a location or depth of bone determined via received ultrasonic energy can be used to guide a probe assembly 334 to a desired insertion location, such as for aiding in administering spinal anesthesia or during a spinal diagnostic procedure. As in the examples of FIGS. 2A-B, the angle of the probe guide 330 can be fixed or adjustable, such as to provide a desired or specified insertion angle to guide the probe (e.g., a needle or catheter) to a desired location and depth in the subject. In an example, the apparatus 300 can include a housing 326 configured to at least partially contain the ultrasonic transducers 312A-D, the probe guide 330, or other circuitry or modules, such as shown in the examples of FIGS. 1 and 2A-B. In an example, the apparatus 300 can include one or more portions of the examples of FIG. 4, such as to aid in locating or visualizing a position of a needle 338 included as a portion of the probe assembly 334, such as before or during a probe insertion procedure.

Figure 4:
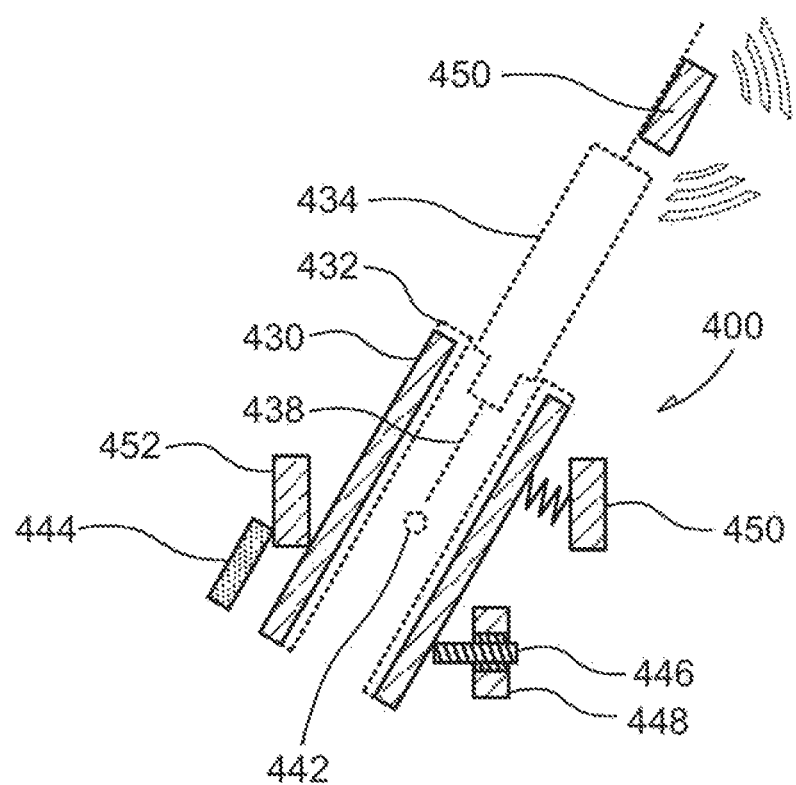
FIG. 4 illustrates generally an example of a probe guide and related apparatus, such as can be included in the examples of FIGS. 1, 2A-B, 3A-B, or other examples.

FIG. 4 illustrates generally an example 400 of a probe guide 430 and related apparatus, such as can be included in the examples of FIGS. 1, 2A-B, 3A-B, or other examples. In an example, a replaceable or removable insert or seal, such as a seal 432, can be positioned along or within a portion of the probe guide 430, such as to isolate a sterile portion of a probe assembly 434, such as a needle or catheter tip 438, from surrounding non-sterile portions of an assembly. The seal 432 may be adhesively coated, or retained such as using a clamp, or an interference fit, or using one or more detents included as a portion of the probe guide 430.

In an example, the angle of the probe guide 430 can be adjusted or positioned, either manually by the user, or automatically, such as to provide a desired or specified probe insertion angle. For example, one or more of a setscrew 446, or a spring portion 450 can be used to pivot a channel of the probe guide, such as pivoting around a pin 442 located along the circumference of the probe guide 430, or pivoting around another portion of the probe guide 430. In an example, the setscrew 446 can be retained by a threaded block 448, such as manually adjusted or driven by a mechanical actuator to allow automatic or semi-automatic rotation of the probe guide 430 about the pin 442. One or more stops, such as a stop 452 can constrain the probe guide 430 within a desired range of possible angular positions. In an example, a ball-and-spring apparatus and detents can be used, such as to allow a user to manually position the probe guide 430 in a desired angular position, with the detents indexing the probe guide 430 to specified angles, such as offset from each other by a specified angular increment.

In an example, a piezoelectric element 444, such as located nearby an opening (e.g., nearby an exit port of the probe guide 430), can be used to automatically measure the angle of the probe guide 430, or to provide feedback for automatic probe guide 430 angular control. An initial distance between the center of the piezoelectric element 444 and the opening of the probe guide can be measured before repositioning to provide a frame of reference or baseline, and thus the position of the opening can be tracked via a deviation from the frame of reference or baseline. The angle may be calculated manually or via a processor circuit, such as based on information provided via the piezoelectric element 444. In this manner, depending on the depth of the probe assembly 434 within the guide 430, the angle of the probe guide 430 can be controlled to such as to provide a desired final depth for the needle 438.

For example, a location of a needle 438 or catheter tip can be tracked, such as using a piezoelectric technique separate from the angular position measurement. Other techniques for tracking the probe assembly 434 position, or needle 438 position, can include using optical or magnetic techniques. For example, one or more reference markings can be provided on a portion of the probe assembly 434 that can be visible within or at an entry port of the guide 430 (e.g., a ruler or scale can be imprinted on the probe assembly 434, such as visible to the user during insertion).

Figure 7:
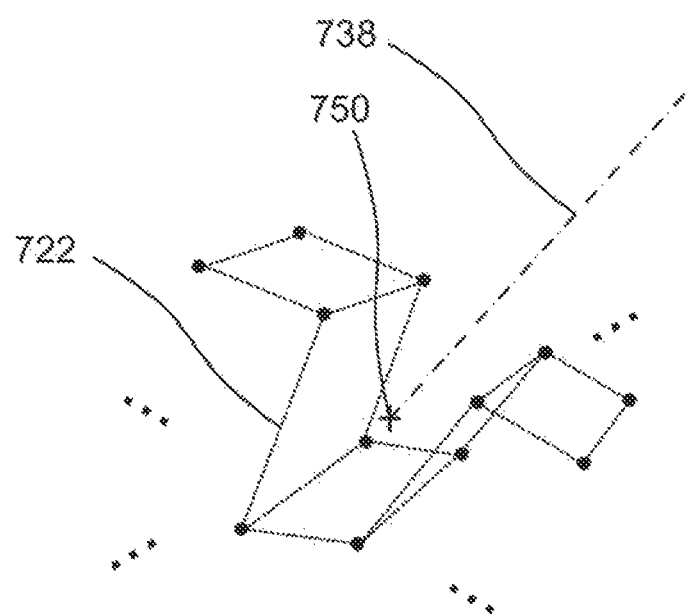
FIG. 7 illustrates generally an illustrative example of information that can be displayed, such as using a portion of the apparatus of FIG. 1, 2A-B, or 3A-B, such as to provide a three-dimensional representation of a location of a target.

In an example, a piezoelectric actuator 450 can be coupled to the needle 438, or another portion of the probe assembly 434. As the probe is inserted into tissue of the subject, one or more techniques can then be used to track the probe tip location, such as via exciting the probe at a known frequency or at a known range of frequencies using the actuator 450, and locating the probe tip using, for example, color Doppler ultrasound techniques. In an example, such as shown in FIG. 7, information about the needle 438 location, within a subject, can be overlaid or otherwise displayed along with other anatomical information, such as to aid a user in positioning the probe tip at a desired location.

In the examples of FIG. 1, 2A-B, 3A-B, or 4, or in other examples, a marking or pinching apparatus can be used in addition to or instead of the probe assembly 434, such as to pinch (e.g., discolor) or mark tissue at a desired probe insertion site, such as using the path provided by the probe guide 430. Such markings or discolorations can be later used by the practitioner to aid in inserting or guiding the probe during a puncture procedure. In an example, a template or patch can be deposited or adhered onto a site of the subject, such as at or near a location of a desired probe insertion site, such as after locating bone or other anatomical features using the hand-held ultrasonic apparatus of the examples of FIG. 1, 2A-B, or 3A-B, or using apparatus or techniques of one or more other examples.

In an example, one or more portions of the example 400 can be separate from the hand-held ultrasonic assembly of FIGS. 1, 2A-B, 3A-C, or as shown and described in other examples. In such an example, the probe tip location can still be tracked using the hand-held apparatus, such as using the piezoelectric or other techniques discussed above. In an example, the hand-held apparatus can be used to mark or otherwise identify an insertion site for the probe, and a separate probe guide apparatus, such as shown in FIG. 4, can be used for insertion of the probe at a desired or specified angle.

FIG. 5 illustrates generally an illustrative example 500 of obtaining information about one or more portions of an anatomy of a subject, such as to assist in determining an insertion location for a probe, or for guiding a probe to a desired location. The apparatus of the previous examples can be used to obtain reflected ultrasonic energy (e.g., echo information) during or after the apparatus is moved from a first position to one or more other positions (or after a portion of the apparatus is mechanically scanned across a range of locations).

A position history along with an echo information history, such as obtained via a hand-held apparatus, can be constructed as multiple echo signals from multiple locations are compiled, such as corresponding to each ultrasound transducer as the apparatus (or a transducer) is translated along a tissue surface. The compiled echo information or data derived from echo information can be used to render an image. The image can include information about an anatomical target location, such as one or more bone locations.

In the example of FIG. 5, two or more ultrasonic transducers can be placed at a specified offset from each other, such as a first transducer 1 and a second transducer 2, such as included on or within a hand-held housing. Bone or other echogenic material can then be detected from returned ultrasound echo information obtained via the transducers 1-2.

In a medical procedure, such as including a probe insertion location for spinal anesthesia or a spinal diagnostic procedure, a desired probe path 538 can include penetration of a suprapspinal ligament 516, just below the skin, along a path 538, through an interpsinal ligament 514 region, and into an epidural space 508 past the ligamentum flavum region, above a first lamina region 504A, and below a second lamina region 504B, between a first portion 510A of the spinous process, or a second portion 510B of the spinous process. The desired final depth of the probe (e.g., a touhy needle, or a catheter), can be near the dura 502 (e.g., for an epidural procedure), or through the dura 502 and into the spinal cavity for other procedures. As discussed in the examples above, the path 538 through the access region between the first and second portions of the spinous processes 510A-B can be angled (e.g., not strictly parallel or perpendicular) with respect to the surface of the skin, and thus one or more of the transducers 1-2 or a probe guide can be positioned at a desired or specified angle to more easily obtain information about the location of the spinous processes 510A-B or the angled access region, or to provide a guide for insertion of a probe along the path 538 at the desired or specified angle.

In an example, such as using two offset ultrasonic transducers 1-2, the position of a hand-held ultrasonic apparatus can be determined with respect to the spinal anatomy (e.g., the first and second portions of the spinous process 510A-B can be determined). For example, a depth of bone beneath the ultrasonic transducers can be estimated from the time required for the acoustic reflection to reach the ultrasonic transducers 1-2.

In an example, a series of acoustic transducers (e.g., transducers 1-2 or other transducers) can be located along two spatial dimensions. The transducers can be arranged, for example, on a fully sampled, two-dimensional grid, or arranged on an arbitrary sparse grid. Similarly, the acoustic transducers may be placed along one spatial dimension and mechanically displaced (e.g., mechanically scanned) to span a two-dimensional area.

In an example, the hand-held assembly can be configured to generate either a focused or unfocused ultrasonic energy, such as delivered via one or more of the transducers 1-2. As sound propagates within tissue, it can be reflected at interfaces between regions having differing acoustic properties. Ultrasound echo signals provided by reflection of ultrasonic energy from bone (e.g., the spinous processes 510A-B) can be of higher amplitude than corresponding echoes provided by surrounding soft tissues, thus offering an opportunity to detect and differentiate the anatomy of interest. In an example, one or more beam-forming techniques can be applied to the echo information. Such techniques can include, for example, delay and sum beam-forming, or adaptive techniques to determine a direction of a dominant signal (e.g., provided by reflection from bone tissue). A processor circuit can implement one or more detection rules, such as to identify echo information corresponding to bone, such as processing radio frequency ultrasonic information using techniques such as comparing the received echo amplitude to a specified threshold, analyzing speckle statistics, analyzing angular scattering characteristics, or matching one or more of received radio frequency data or imaging information to a pattern utilizing a prior knowledge of spinal anatomy.

In the example of FIG. 5, transducers 1-2 can be located in a first region 530, such as along the skin of a subject, such as configured to obtain reflected echo information from the second region of the spinous process 510B. The depth samples as shown in the plot 520 can indicate that the center-line between the transducers 1-2 is located near a shallow portion of the spinous process 510B. In an illustrative example, the transducers 1-2 can be swept along the surface of the skin parallel to the spine (or perpendicular to the spinal axis, in other examples). In a second region 531, the depth samples shown in the plot 520 indicate that the center-line between the transducers is aligned near the access space between the spinous processes 510A-B. As the transducers 1-2 are swept further along the surface of the skin into a third region 532, the depth samples indicate that the center-line between the transducers is located near a shallow portion of the spinous process 510A.

In an example, the acoustic transducers can be coupled to a processor circuit to process echo information obtained from an array of transducers to construct a composite image corresponding to one or more planes A-C that are parallel to the surface of the skin, or parallel to an active surface of the transducer array, to provide a "C-mode" image. With this imaging modality, echo information can be obtained over a plane, such as one or more of planes A-C, that "slices" the spinous processes 510A-B along their protrusions.

Figure 6A:
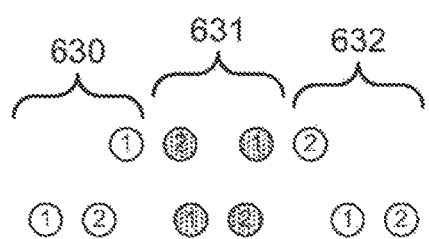
FIGS. 6A-C illustrate generally various illustrative examples of information that can be displayed, such as using a portion of the apparatus of FIG. 1, 2A-B, or 3A-B, such as to provide information about a location of a target, such as corresponding to the illustrative example of FIG. 5.
Figure 6B:
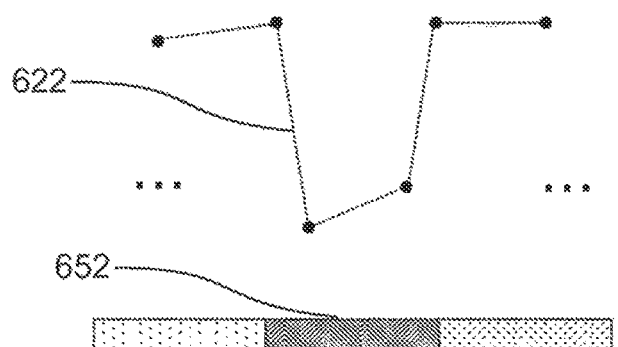
Figure 6C:

FIGS. 6A-C illustrate generally various illustrative examples of information that can be displayed, such as using a portion of the apparatus of FIG. 1, 2A-B, or 3A-B, such as to provide information about a location of a target, such as corresponding to the illustrative example of FIG. 5.

A simple, intuitive display can be configured to indicate a presence or absence of bone within a specified or adjustable depth from the transducers 1-2, such as via one or more indicators on a display, such as shown in the example of FIG. 6A. For example, a first indicator 1 can be lit (or shaded, colored, or an indicator can be shown on a pixel-based display, etc.) when a depth sample obtained via the first transducer 1 indicates bone within a specified range of the first transducer 1, such as in a first state 630 corresponding to a location of the transducers 1-2 in the first region 530 of FIG. 5. Because the spinous process 510B is shallow with respect to both transducers 1-2 in the first region 530, both indicators 1-2 in FIG. 6 can be lit. In an illustrative example, as the transducers 1-2 of FIG. 5 are swept or moved along the spine, the second indicator 2 in FIG. 6 will first go out, but the first indicator 1 in FIG. 6 can remain lit. As the transducers 1-2 of FIG. 5 pass through the second region 531, both the first and second indicators 1-2 go out, in the second state 631, indicating to the user that the transducers are centered on the access space between the spinous processes 510A-B. As the transducers 1-2 are further swept along the spine, they again detect shallow bone in the third region 532, and both the indicators are again lit in the third state 632 of FIG. 6.

In an example, such as shown in FIGS. 3A-B, a probe guide can be included along the center line (or at another specified location) with respect to the transducers 1-2 of FIG. 5. The user can move the hand-held ultrasonic apparatus around the skin near the spinal anatomy, such as marking the locations along the subject where the indicators show shallow bone, or inserting the probe at a location where the indicators show alignment with the region between the spinous processes 510A-B.

In addition to the indicators of FIG. 6A, a display can be used to present a composite representation of the underlying spinal or bone anatomy, such as two-dimensional representation 622 as shown in FIG. 6B, or using coloring or shading to indicate deep or shallow dominant echo return depths, such as shown in the example 652 of FIG. 6C. One or more of the representation 622 of FIG. 6B, or the example 652 of FIG. 6C can be aligned with a portion of the hand-held assembly, such as updated in response to changes in the position of the hand-held assembly. In an example, the shaded rendering of the example 652 can correspond to an approximate surface rendering of the spinal anatomy, with the rendering appearing coarse, or updated to become more refined as more depth samples are acquired (e.g, via repositioning of the hand-held apparatus, or via mechanical scanning of the transducers 1-2 of FIG. 5).

FIG. 7 illustrates generally an illustrative example of information that can be displayed, such as using a portion of the apparatus of FIG. 1, 2A-B, or 3A-B, such as to provide a three-dimensional representation 722 of a location of a target.

In an example, a composite ultrasound image constructed from received echo information can be displayed to show the location of the spinous processes and a path 738 along a region for probe access. In the example including a depth sampling technique, a spline or other technique can be used to create a three-dimensional map of sampled depths, such as using information about motion of the hand-held assembly provided by a motion-tracking circuit. In the example of "C-mode" imaging, received echo information corresponding to different planes can be processed to construct a three-dimensional map of the anatomical region of interest.

In an example, the echo information can be processed to output intuitive indicators or text providing feedback about a region that can be used for probe access, without the need for user interpretation of ultrasound images, such as discussed above in the example of FIG. 6A. In the example of FIG. 7, a probe tip location 750 can be estimated or determined automatically such as using one or more techniques discussed above, such a location 750 overlaid on the three-dimensional rendering 722.

While the examples of FIGS. 5, 6A-C and 7 refer generally to location of an access region for spinal anesthesia or a spinal diagnostic procedure, similar techniques can be used for locating other bone structures, such as for aiding in locating or guiding a needle to access one or more other anatomical regions. Such regions can include a compartment or region next to one or more other vertebral or spinal structures. Such an example can include guiding insertion of a probe during or before a paravertebral somatic nerve blockade (PVB), or one or more other procedures. In a PVB example, the techniques of FIG. 5, 6A-C, or 7 (or other examples such as using the apparatus of FIG. 1, 2A-B, or 3A-B) can be used to aid in locating bone surrounding a paravertebral space, such as to aid a user in locating an insertion point on the skin for a probe (e.g., a needle) or in guiding a needle or catheter to the paravertebral space.

Figure 8:
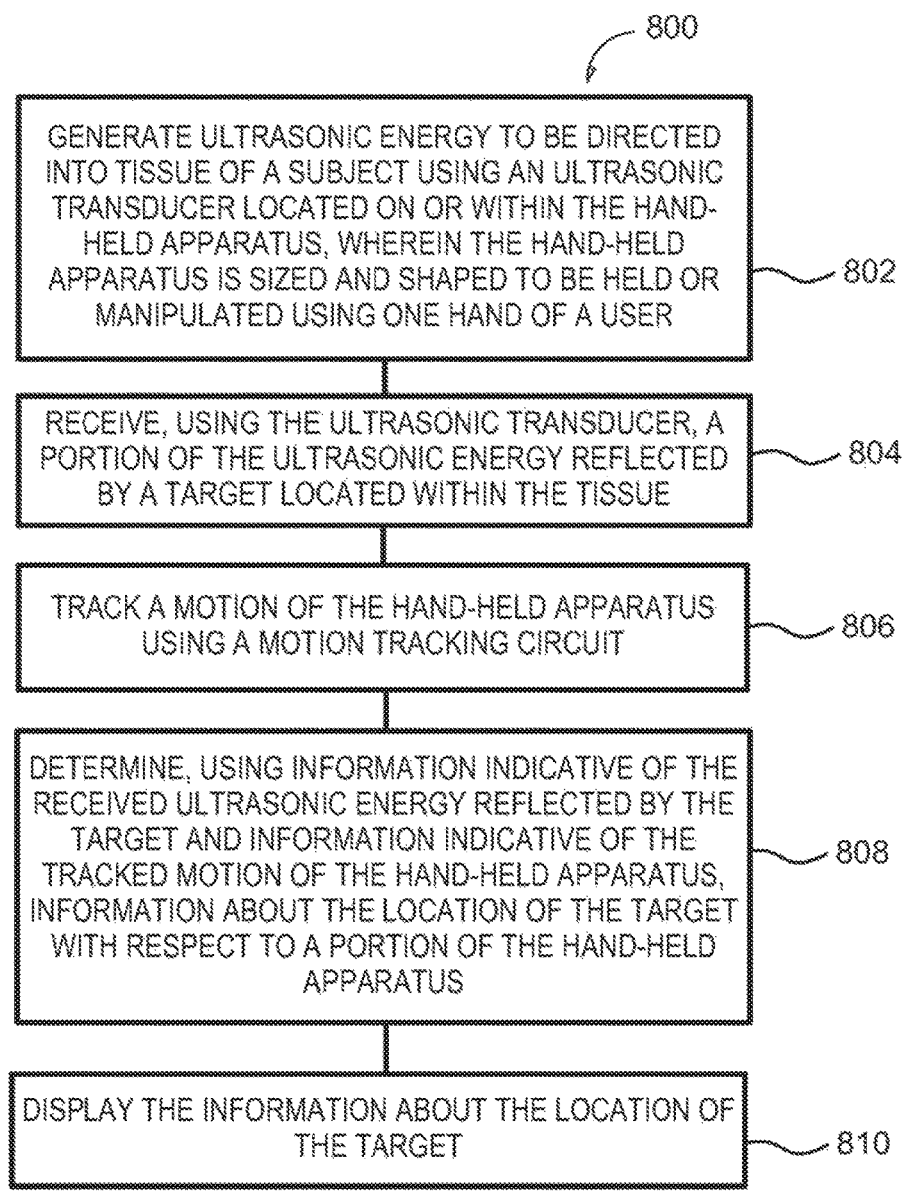
FIG. 8 illustrates generally an example of a technique that can include generating ultrasonic energy to be directed into tissue of a subject.

FIG. 8 illustrates generally an example of a technique 800 (e.g., a method, or instructions stored on a computer readable medium, such as a memory circuit, that can be performed by a processor circuit). At 802, the technique 800 can include generating ultrasonic energy to be directed into tissue of a subject, such as using an ultrasonic transducer located on or within a hand-held apparatus. The hand-held apparatus can be sized and shaped to be held or manipulated using one hand of a user, such as discussed in relation to the apparatus or techniques of the examples above. At 804, ultrasonic energy can be received, such as using the ultrasonic transducer that had been used to generate the ultrasonic energy directed into the subject. At 806, motion of the hand-held apparatus can be tracked, such as using a motion tracking circuit as discussed in the examples above. At 808, information about a location of a target (e.g., bone, such as a portion of the spinal process) can be determined, using information indicative of the received ultrasonic energy reflected by the target and information indicative of the tracked motion of the hand-held apparatus. In an example, the technique 800 can include displaying information about the location of the target.

Figure 9:
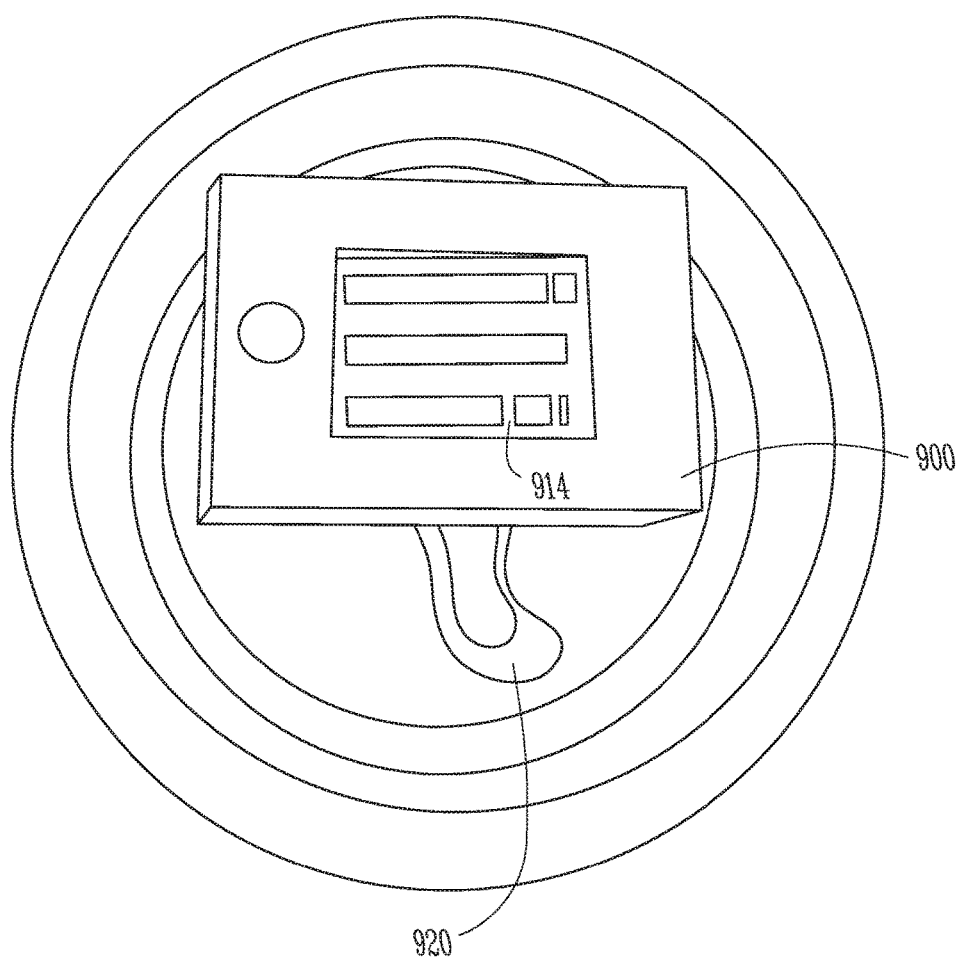
FIG. 9 illustrates generally an illustrative example of a hand-held apparatus that can include multiple ultrasonic transducers, and a display configured to provide information about a location of a target at least in part using ultrasonic energy reflected from the target.

FIG. 9 illustrates generally an illustrative example of a photograph of hand-held apparatus 900 that can include multiple ultrasonic transducers, and a display 914 configured to provide information about a location of a target 920 at least in part using ultrasonic energy reflected from the target. In the example of FIG. 9, the transducers can be offset from each other similarly to the example of FIGS. 2A-B or FIGS. 3A-B. It is believed that bone or other echogenic material can provide a bright signature (e.g., one or more "A-lines") such as shown on the display 914, and the display 914 can provide information about the location of the bone. In the example of the A-line display 914 of the FIG. 9, the position of the line along the display can indicate the delay, and thus the depth, of the received echo, and one or more of the color or displayed brightness of the line can indicate the intensity of the received echo. As discussed in the previous examples, such depth information can be determined automatically, such as to construct a composite two- or three-dimensional representation of a target (e.g., bone) structure, such as using the reflected ultrasonic energy corresponding to hyperechoic bone or another echogenic target.

Various Notes & Examples

Example 1 includes subject matter, such as an apparatus, comprising a housing sized and shaped to be held or manipulated using one hand of a user, an ultrasonic transducer located on or within the housing and configured to generate ultrasonic energy directed into tissue of a subject and configured to receive a portion of the ultrasonic energy reflected by a target located within the tissue, a processor circuit configured to control the ultrasonic transducer to generate or receive ultrasonic energy and configured to obtain information indicative of the ultrasonic energy reflected by the target, a motion tracking circuit configured to provide information indicative of a motion of at least a portion of the hand-held apparatus to the processor circuit, and a display configured to present information about a location of the target with respect to a portion of the hand-held apparatus, the information about the location determined by the processor circuit using the obtained information indicative of the ultrasonic energy reflected by the target and the information indicative of the motion of the hand-held apparatus obtained from the motion tracking circuit.

In Example 2, the subject matter of Example 1 can optionally include a target comprising bone, and a display configured to present information indicative of a position of the bone with respect to a portion of the hand-held apparatus.

In Example 3, the subject matter of one or any combination of Examples 1-2 can optionally include a display configured to provide information indicative of a first depth of the target at a first location using obtained information indicative of the ultrasonic energy reflected by the target, the display configured to provide information indicative of a second depth of the target at a second location using the obtained information indicative of the ultrasonic energy reflected by the target.

In Example 4, the subject matter of one or any combination of Examples 1-3 can optionally include a first ultrasonic transducer configured to receive ultrasonic energy from a specified range of depths including the first depth, and a second ultrasonic transducer configured to receive ultrasonic energy from a specified range of depths including the second depth, the active surfaces of the first and second ultrasonic transducers laterally separated from each other along a face of the housing.

In Example 5, the subject matter of one or any combination of Examples 1-4 can optionally include a processor circuit configured to construct a composite image of the target for presentation to the user via the display, using information indicative of the ultrasonic energy reflected by the target obtained when the hand-held apparatus is located in a first position along the subject, and obtained during or after movement of the hand-held apparatus to a second position.

In Example 6, the subject matter of one or any combination of Examples 1-5 can optionally include a processor circuit configured to construct the composite image to include a two-dimensional representation of the target, the representation including an indicator of one or more of a first depth of the target at the first location or a second depth of the target at the second location.

In Example 7, the subject matter of one or any combination of Examples 1-6 can optionally include a processor circuit configured to construct a composite image including a three-dimensional representation of the target.

In Example 8, the subject matter of one or any combination of Examples 1-7 can optionally include a processor circuit configured to update a location of the target indicated on the display as the hand-held apparatus is moved, using information obtained from the motion tracking circuit.

In Example 9, the subject matter of one or any combination of Examples 1-8 can optionally include a guide configured to provide a specified path for guiding travel by a probe, the guide comprising an entry port configured for insertion of the probe into the guide by a user, and an exit port configured to provide an insertion location for the probe along the subject.

In Example 10, the subject matter of one or any combination of Examples 1-9 can optionally include a probe comprising a catheter or a needle.

In Example 11, the subject matter of one or any combination of Examples 1-10 can optionally include a sterile seal configured to isolate the probe, or the subject, from a non-sterile portion of the apparatus.

In Example 12, the subject matter of one or any combination of Examples 1-11 can optionally a guide having an angular positioning portion configured to pivot the guide to provide a specified insertion angle for the probe.

In Example 13, the subject matter of one or any combination of Examples 1-12 can optionally include a probe position sensor configured to provide information indicative of one or more of a probe angle or a probe depth, to the processor circuit, the processor circuit configured to provide on the display information indicative of a position of the probe using information indicative of one or more of the probe angle or probe depth obtained from the probe position sensor.

In Example 14, the subject matter of one or any combination of Examples 1-13 can optionally include an ultrasonic transducer configured to be mechanically scanned, and a motion tracking circuit configured to provide information indicative of a motion of the ultrasonic transducer.

Example 15 can include, or can optionally be combined with the subject matter of one or any combination of Examples 1-14 to include, subject matter (such as a method, a means for performing acts, or a machine-readable medium including instructions that, when performed by the machine, cause the machine to perform acts) comprising generating ultrasonic energy to be directed into tissue of a subject using an ultrasonic transducer located on or within the hand-held apparatus, wherein the hand-held apparatus is sized and shaped to be held or manipulated using one hand of a user, receiving, using the ultrasonic transducer, a portion of the ultrasonic energy reflected by a target located within the tissue, tracking a motion of at least a portion of the hand-held apparatus using a motion tracking circuit, determining, using information indicative of the received ultrasonic energy reflected by the target and information indicative of the tracked motion of the hand-held apparatus, information about the location of the target with respect to a portion of the hand-held apparatus, and displaying the information about the location of the target.

In Example 16, the subject matter of Example 15 can optionally include a target comprising bone, and displaying the information including presenting information indicative of a position of the bone with respect to a portion of the hand-held apparatus.

In Example 17, the subject matter of one or any combination of Examples 15-16 can optionally include determining a first depth of the target at a first location using the information indicative of the ultrasonic energy reflected by the target, determining a second depth of the target at a second location using the information indicative of the ultrasonic energy reflected by the target, and displaying information indicative of the first depth at the first location, and the second depth at the second location.

In Example 18, the subject matter of one or any combination of Examples 15-17 can optionally include constructing a composite image of the target for presentation to the user, using information indicative of the ultrasonic energy reflected by the target obtained when the hand-held apparatus is located in a first position along the subject, and obtained during or after movement of the hand-held apparatus to a second position.

In Example 19, the subject matter of one or any combination of Examples 15-18 can optionally include constructing a composite image to include a two-dimensional representation of the target, the representation including an indicator of one or more of a first depth of the target at the first location or a second depth of the target at the second location.

In Example 20, the subject matter of one or any combination of Examples 15-19 can optionally include constructing a composite image to include a three-dimensional representation of the target.

In Example 21, the subject matter of one or any combination of Examples 15-20 can optionally include updating a location of the target indicated on the display as the hand-held apparatus is moved, using information indicative of the tracked motion of the hand-held apparatus.

In Example 22, the subject matter of one or any combination of Examples 15-21 can optionally include sensing one or more of a probe angle or probe depth of a probe within a guide, the guide comprising a portion of the hand-held apparatus, the guide comprising an entry port configured for insertion of the probe into the guide by a user, and an exit port configured to provide an insertion location for the probe along the subject.

In Example 23, the subject matter of one or any combination of Examples 15-22 can optionally include displaying information indicative of a position of the probe using information indicative of one or more of a sensed probe angle or a sensed probe depth.

In Example 24, the subject matter of one or any combination of Examples 1-23 can optionally include mechanically scanning the ultrasonic transducer, and tracking the motion of the ultrasonic transducer using a motion tracking circuit.

Example 25 includes subject matter, such as an apparatus, comprising a housing sized and shaped to be held or manipulated using one hand of a user, an ultrasonic transducer located on or within the housing and configured to generate ultrasonic energy directed into tissue of a subject and configured to receive a portion of the ultrasonic energy reflected by a target located within the tissue, a processor circuit configured to control the ultrasonic transducer to generate or receive ultrasonic energy and configured to obtain information indicative of the ultrasonic energy reflected by the target, a motion tracking circuit configured to provide information indicative of a motion of at least a portion of the hand-held apparatus to the processor circuit, and a display configured to present information about a location of the target with respect to a portion of the hand-held apparatus, the information about the location determined by the processor circuit using the obtained information indicative of the ultrasonic energy reflected by the target and the information indicative of the motion of the hand-held apparatus obtained from the motion tracking circuit, the processor circuit configured to construct a composite image of the target for presentation to the user via the display, using information indicative of the ultrasonic energy reflected by the target obtained when the hand-held apparatus is located in a first position along the subject, and obtained during or after movement of the hand-held apparatus to a second position.

Example 26 can include, or can optionally be combined with any portion or combination of any portions of any one or more of Examples 1-25 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A hand-held apparatus, comprising:
   a hand-held housing having a planar surface;
   a probe guide configured to provide a specified path for guiding travel by a probe, the guide extending along a central axis from an entry port to an exit port, the entry port configured for insertion of the probe into the probe guide by a user, the exit port configured to provide an insertion location for the probe in a subject, the exit port disposed proximal to the planar surface;
   a piezoelectric element disposed proximal to the probe guide and configured to measure an angle of the central axis of the probe guide;
   one or more ultrasonic transducers located on or within the hand-held housing and configured to generate ultrasonic energy directed into tissue of the subject at an angle parallel to the central axis of the probe guide, and configured to receive ultrasonic energy reflected by a target, including underlying bone and an access site adjacent to the underlying bone;
   a motion tracking circuit included in the housing and configured to provide information indicative of a motion of the hand-held apparatus when the hand-held apparatus is mechanically scanned by the user;
   a processor circuit configured to:
   determine information about a relative location of the underlying bone and the access site with respect to a portion of the hand-held apparatus using the received ultrasonic energy and the information indicative of the motion of the hand-held apparatus; and
   calculate the angle of the probe guide from an output of the piezoelectric element; and
   a display mounted on or within the housing and configured to receive and display the determined information from the processor circuit; wherein
   the information about the relative location of the underlying bone with respect to the portion hand-held apparatus includes information about a relative surface position of the underlying bone with respect to the portion of the hand-held apparatus and information about a relative orientation of the underlying bone with respect to the portion of the hand-held apparatus; and wherein
   the probe guide includes a mechanical actuator configured to automatically adjust the angle of the probe guide according to the calculated angle and the determined information.

2. The hand-held apparatus of claim 1, wherein the information about a relative location of the underlying bone includes information indicative of first and second depths of the underlying bone at respective first and second locations; and the display is configured to provide the information of the first and second depths of the underlying bone at respective first and second locations using coloring or shading.

3. The hand-held apparatus of claim 2, wherein the one or more ultrasonic transducers comprises a first ultrasonic transducer focused to receive ultrasonic energy from a specified range of depths including the first depth, and a second ultrasonic transducer focused to receive ultrasonic energy from a specified different range of depths including the second depth, and wherein active surfaces of the first and second ultrasonic transducers are laterally separated from each other along a face of the housing.

4. The hand-held apparatus of claim 1, wherein the processor circuit is configured to construct a composite image of the underlying bone for presentation to the user via the display using received ultrasonic energy obtained when the hand-held apparatus is moved from a first position to a second position.

5. The hand-held apparatus of claim 4, wherein the processor circuit is configured to construct the composite image to include a two-dimensional representation of the bone along with an indicator of one or more of a first depth of the underlying bone at the first location or a second depth of the underlying bone at the second location.

6. The hand-held apparatus of claim 4, wherein the processor circuit is configured to construct the composite image to include a three-dimensional representation of bone.

7. The hand-held apparatus of claim 1, wherein the processor circuit is configured to update the information about the relative location of the bone as the hand-held apparatus is moved using the information from the motion tracking circuit.

8. The hand-held apparatus of claim 1, wherein the probe includes a catheter or a needle.

9. The hand-held apparatus of claim 1, comprising a sterile seal configured to isolate the probe, or the subject, from a non-sterile portion of the apparatus.

10. The hand-held apparatus of claim 1,
wherein the processor circuit is configured to provide on the display information indicative of a position of the probe using information indicative of the angle of the probe obtained from the piezoelectric element.

11. A hand-held apparatus comprising:
a hand-held housing having a planar surface;
a probe guide configured to provide a specified path for guiding travel by a probe, the guide extending along a central axis from an entry port to an exit port, the entry port configured for insertion of the probe into the guide by a user, the exit port configured to provide an insertion location for the probe in a subject, the exit port disposed proximal to the planar surface;
one or more angled ultrasonic transducers located on or within the housing and configured to generate ultrasonic energy directed into tissue of a subject including energy directed at an angle parallel to the central axis of the probe guide included as a portion of the hand-held apparatus, and configured to receive the ultrasonic energy reflected by a target, including bone and an access site adjacent to the bone, located within the tissue;
a piezoelectric element disposed proximal to the probe guide and configured to measure an angle of the central axis of the probe guide;
a motion tracking circuit included in the housing and configured to provide information indicative of a motion of the hand-held apparatus when the hand-held apparatus is mechanically scanned by a user;
a processor circuit configured to:
determine information about a relative location of the bone and the access site with respect to a portion of the hand-held apparatus using the received ultrasonic energy reflected by the target and the information indicative of the motion of the hand-held apparatus; and
calculate the angle of the probe guide from an output of the piezoelectric element; and
a display mounted on or within the housing and configured to receive and display the determined information from the processor circuit; wherein
the processor circuit is further configured to construct a composite image of the bone for presentation to the user via the display, the composite image including information about a relative surface position of the bone with respect to the probe guide and information about a relative orientation of the bone with respect to the probe guide, using ultrasonic energy reflected by the target obtained when the hand-held apparatus is located in a first position along the subject, and ultrasonic energy reflected by the target obtained during or after movement of the hand-held apparatus to a second position, as the apparatus is mechanically scanned by the user; and wherein the probe guide includes a mechanical actuator configured to automatically adjust the angle of the probe according to the calculated angle and the determined information.

12. The hand-held apparatus of claim 11, wherein the one or more angled ultrasonic transducers comprises a first ultrasonic transducer focused to receive ultrasonic energy from a specified range of depths including the first depth, and a second ultrasonic transducer focused to receive ultrasonic energy from a specified range of depths including the second depth, wherein active surfaces of the first and second ultrasonic transducers are laterally separated from each other along a face of the housing, and wherein the first and second ultrasonic transducers are mounted at an angle neither parallel nor perpendicular to the plane parallel to the planar surface of the hand-held housing.

13. The hand-held apparatus of claim 3, wherein the first and second ultrasonic transducers are mounted at an angle neither parallel nor perpendicular to the plane parallel to the planar surface of the hand-held housing.

14. The hand-held apparatus of claim 1, wherein the processor circuit is configured to control the angle of the probe guide to provide a desired final depth for a probe.

15. The hand-held apparatus of claim 11, wherein the processor circuit is configured to control the angle of the probe guide to provide a desired final depth for a probe.

* * * * *